United States Patent [19]

Steer et al.

[11] Patent Number: 4,518,389
[45] Date of Patent: May 21, 1985

[54] INTERDIGITATED COUPLING FOR AN OSTOMY BAG

[75] Inventors: Peter L. Steer; John V. Edwards, both of East Grinstead, England

[73] Assignee: Kingsdown Medical Consultants, Limited, London, England

[21] Appl. No.: 591,727

[22] Filed: May 2, 1984

Related U.S. Application Data

[63] Continuation of Ser. No. 374,455, May 3, 1982, abandoned.

[30] Foreign Application Priority Data

Jun. 26, 1981 [GB] United Kingdom ............... 8119731

[51] Int. Cl.³ ............................................. A61F 5/44
[52] U.S. Cl. ................................................ 604/339
[58] Field of Search .................. 604/304, 332–344, 604/277; 285/110, 331, DIG. 14, DIG. 22; 24/204, 329, 385, 442

[56] References Cited

U.S. PATENT DOCUMENTS

| | | | |
|---|---|---|---|
| 2,499,898 | 3/1950 | Anderson | 24/442 |
| 3,339,546 | 9/1967 | Cher | 604/304 |
| 3,808,648 | 5/1974 | Billarant et al. | 24/204 |
| 3,913,183 | 10/1975 | Brumlik | 24/442 |
| 3,923,213 | 12/1975 | George et al. | 24/442 |
| 3,961,398 | 6/1976 | Herterich et al. | 24/204 |
| 3,970,085 | 7/1976 | Mersan | 604/339 |
| 4,078,567 | 3/1978 | Fenton | 604/342 |
| 4,169,303 | 10/1979 | Lemelson | 24/204 |
| 4,232,672 | 11/1980 | Steer et al. | 604/338 |

FOREIGN PATENT DOCUMENTS

1218237  6/1966  Fed. Rep. of Germany ...... 285/331

Primary Examiner—C. Fred Rosenbaum
Assistant Examiner—J. L. Kruter
Attorney, Agent, or Firm—Lawrence S. Levinson; Sanford J. Asman

[57] ABSTRACT

A coupling for an ostomy bag is described. The coupling includes a pair of cylindrical elements which each have a headed pin attachment means mounted on a respective flange. An interdigitation of pins and heads secures the cylindrical elements to one another. One of the coupling elements is adhesively attached to a wearer, and the other coupling element has an ostomy bag attached to it. Thus, an ostomy bag may be readily and securely attached to a user through the use of the present invention.

6 Claims, 3 Drawing Figures

INTERDIGITATED COUPLING FOR AN OSTOMY BAG

This is a continuation of application Ser. No. 374,455, filed May 3, 1982, now abandoned.

BACKGROUND OF THE INVENTION

This invention relates to a coupling for fixing an ostomy bag to an adhesive pad or dressing worn by a person who has had surgery, such as an ileostomy, a colostomy, or a urostomy.

In British Patent Specification No. 751 333 of Tasse, a bag-support disc is described which has a central opening surrounded by a collar. The collar cooperates with a beading provided at the mouth of an ostomy bag. A carrier disc entraps the bag mouth and secures it to the bag supporting disc. It is not believed that the device described by Tasse has enjoyed any wide acceptance among users, probably because of sealing difficulties and the expense and impracticability of moulding an individual article for each user.

In British Patent Specification No. 760 939, published in 1956, Galliard, described a design for a urinal which is not appropriate for ostomy use. In British Patent Specification No. 839 818, published in 1960, Jacobsen et al. described a flange bearing an adhesive layer which could be stuck onto colostomy patents. The flange extends from a bushing or collar to which a bag mouth may be attached. This arrangement involves a significant insecurity of attachment, with a high risk of leakage. British Patent Specification No. 1 021 145 describes a connector that a bag can be readily attached to and removed from. However, the apparatus requires two separate operations. Before replacing the bag, one must unscrew the connector to which the bag is attached from the fitting which is secured to the body. That operation involves a risk of leakage, as it is necessary to invert the bag. Also, it is an awkward operation to perform, as the bag is either full, or partially full, of bodily waste products. Therefore, manipulation of the couplings will be an unpleasant operation even if, as is often not the case, the user has a high degree of dexterity.

British Patent Specification No. 1 099 455 describes an appliance having a ring which cooperates with a partial ring used to trap the neck of a bag when the ring and partial ring are engaged with the mouth of the bag between them. If adequate security against leakage is to be provided, it is necessary that the ring and partial ring fit tightly together. However, this makes it difficult for the user to pull off the partial ring. As the partial ring is pulled off, the pulling action can impair the security of attachment of the ring to the surgical dressing, or it can impair the security of the dressing to the skin of the wearer. Also, discomfort to the wearer may result.

In British Patent Specification No. 1 212 904, a complicated approach is described. A clamping ring which has a ring-closing lever associated with it embraces the mouth of a bag. The clamping ring is used to clamp the bag mouth to an annular shoulder of a member which is held against the user's body by a belt. Such an apparatus is relatively complicated, and it is not suitable for mass production. In addition, removal of a full bag without spillage requires care and skill, and is especially difficult for old or infirm patients. Thus, there is still an unsatisfied need for a design which allows quick and easy bag changing with reduced risk of spillage.

British Patent Specification No. 1 139 715 describes an earlier invention by one of the inventors herein. That invention is a plain flat resilient pad or disc of a foam plastic material which is attached to the patient by adhesive.

British Patent Specification No. 1 445 784, published in 1976, and assigned to Howmedica Inc., describes a stoma drainage appliance which includes a face plate and an aperture insert. The elastic mouth of a bag is stretched over a skirt on the face plate. Aperture inserts of different sizes are provided according to the desired size of the opening which is to accommodate the stoma. It is believed that this arrangement also involves an unacceptable risk of leakage.

A very successful system is described in British Patent Specification No. 1 571 657 of Kingsdown. However, in certain circumstances the coupling described therein is undesirably rigid. It would be desirable to provide a coupling having the good sealing and easy manipulation characteristics of that coupling while also providing improved flexibility.

SUMMARY OF THE INVENTION

According to the present invention, there is provided a coupling for joining an ostomy bag to a pad of adhesive material which can be applied to the wearer of the bag. The coupling includes two coupling elements, each of which has a substantially cylindrical, hollow portion. An annular flange extends laterally from each of the coupling elements. One of the elements has an internal flexible sealing skirt which is an integral part of the cylindrical, hollow portion of that element. The sealing skirt is configured to make sealing engagement with the external surface of the cylindrical, hollow portion of the other coupling element. Each of the flanges has projecting therefrom in a substantially axial direction, a plurality of pins. The pins have a head configuration adapted to engage with a similar pin.

With the present apparatus, one coupling element is fixed in any convenient way to a pad of skin-compatible adhesive material. The other coupling element is fixed in any convenient way to an ostomy bag. The bag has a hole in one of its walls which the flange of the coupling element surrounds. When the coupling elements are brought together in an axial direction with one cylindrical, hollow portion extending inside the other, the headed pins on the flange of one coupling element interdigitate with the headed pins on the flange of the other coupling element and hold the two coupling elements together. At the same time, the distribution of the pins over the flanges allows the coupled elements to flex to a limited extent, thereby making wearing the device more comfortable.

In a preferred embodiment of the invention, both coupling elements are made of a flexible plastic. Also, as a preferred feature, the pins are integral with their respective flanges, and the flanges are integral with the respective cylindrical portions.

The shape of the heads of the pins is not critical. The pin heads may be rounded, or hemispherical, as are the pins shown in U.K. patent application Ser. No. 2 027 794A and in U.S. Pat. No. 4,216,257 entitled STRIP MATERIAL FOR FORMING FLEXIBLE BACKED FASTENERS which issued to R. T. Schams, et al. on Aug. 5, 1980. Alternatively, they may be conical, wedge-shaped, or pyramidal. Any construction which can be manually engaged and disengaged by the user without awkward manipulation and the application of high pulling forces will be satisfactory.

The flexible sealing skirt may, in particular, be circumferentially located around the internal surface of the outer coupling element.

DETAILED DESCRIPTION OF THE PREFERRED EMBODIMENT

Figure 1:
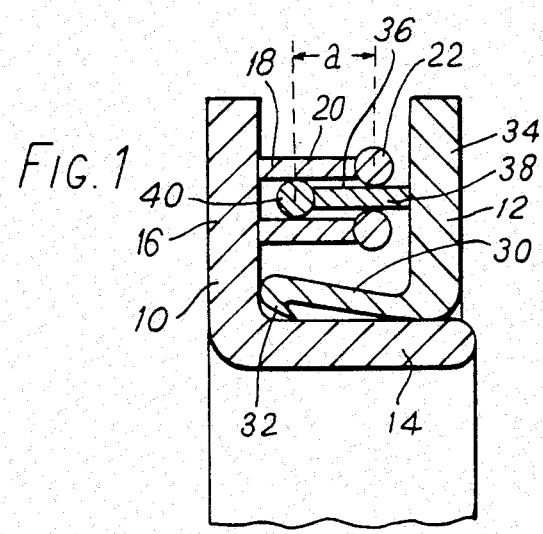
FIG. 1 is a cross-section of one embodiment of the coupling elements of the present invention, in coupled condition.
Figure 2:
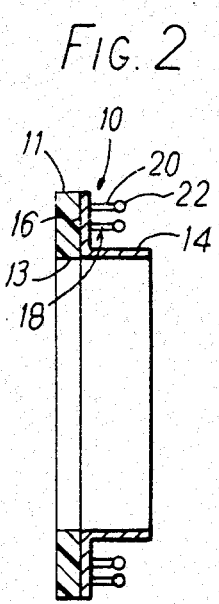
FIG. 2 is a cross-section through one embodiment of an inner, or male, coupling element according to the present invention.
Figure 3:
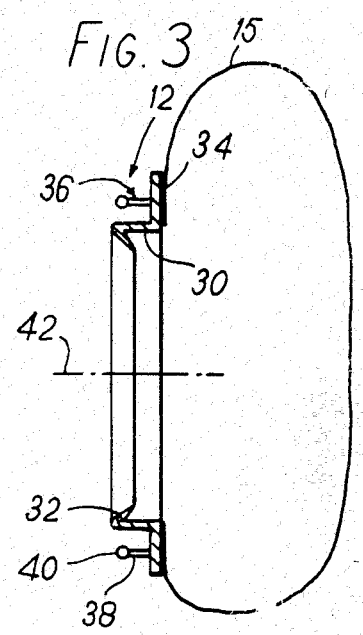
FIG. 3 is a like view of an outer or female, coupling element complementary to the element shown in FIG. 2.

Referring generlly to FIGS. 1-3, the present invention comprises a male, or inner coupling element 12 which is complementary to and cooperates with an outer, or female, coupling element 10. It is preferred that one of the elements, i.e. the female element 10, be fixed to the wearer, for example, by an adhesive pad 11 of a suitable skin-compatible dressing. One such skin-compatible dressing is described in U.S. Pat. No. 3,339,546 entitled BANDAGE FOR ADHERING TO MOIST SURFACES which issued to J. L. Chen on Sept. 5, 1967. The dressing described therein is commercially available from E. R. Squibb and Sons, Inc. and is known by the Registered Trademark "Stomahesive". Such a pad 11 will, of course, have a central aperture 13, therein to allow passage of excretions of the wearer therethrough. With the element 10 attached to the pad 11, and the pad 11 adhesively attached to the wearer, the element 12 is attached to a wall of a conventional ostomy bag 15. The wall must, of course, have a corresponding aperture to permit any body excretions leaving the stoma to pass into the ostomy bag 15.

The coupling element 10 includes a cylindrical portion 14 and a laterally extending flange 16. The flange 16 carries a number of headed pins 18, each pin 18 having a shank 20 and a head 22. As illustrated, the heads 22 are substantially spherical. These pins 18 are arranged in two circumferential rows, spaced apart in a radial direction by a distance such that the minimum distance between two adjacent pin heads 22 is less than the diameter of the head 40 of a pin 36 on the other coupling element 12.

The outer coupling element 12 includes a cylindrical portion 30 having a flexible, resilient sealing skirt 32 which extends inwardly therefrom. The cylindrical portion 30 is integral with a laterally extending flange 34. The flange 34 carries a row of headed pins 36 each having a shank 38 and a substantially spherical head 40. The pins 36 are located in a row having a radial distance from the axis 42 of the coupling 12 such that the pins 36 can be pushed between the two rows of pins 18 on the coupling element 10 when the two coupling elements 10, 12 are assembled together, as best seen in FIG. 1.

By way of example, the shank 20 of each pin 18 may be of substantially cylindrical shape and may have a diameter of approximately 0.040 inches. Similarly, the head 22 of each pin 18 may be substantially spherical in shape and may have a diameter of approximately 0.055 inches. The spacing between the adjacent rows of pins 18 on the coupling element 10, measured in a radial direction between the centers of these rows may, for example, be substantially 0.095 inches. Of course, other dimensions may be employed, and it is not essential that the pin shanks 20 be cylindrical nor that the pin heads 22 be spherical. Thus, a pin with a shank of square cross-section and a pyramidal head, or other configurations, would be equally suitable.

The inclined tapering sealing skirt 32 engages, as seen best in FIG. 1, against the exterior surface of the cylindrical portion 14, thereby providing a good liquid seal therebetween. It has been unexpectedly found that this seal remains effective even though the assembled coupling is twisted or deformed, as may occur, for example, while it is being worn. It will be realized that there is a degree of freedom for the coupling elements to move apart by the distance indicated at "a" in FIG. 1, before any likelihood of disengagement of the two coupling elements 10, 12 occurs. Also, flexibility is introduced into the assembled coupling by virtue of the fact that the shanks of the pins, which are made of plastic, can be bent to some extent.

In a preferred embodiment of the invention, each coupling element is separately moulded as an integral piece of plastic. As an alternative, a strip of material of the kind shown in U.S. Pat. No. 4,216,257 could be arranged circumferentially around each flange with the heads of the pins pointing towards each other, as indicated in FIG. 1. Such strips could be adhesively secured to the respective flanges which support them.

It will be seen from the foregoing disclosure that a novel and useful coupling element for use with ostomy bags has been provided which allows improved flexibility while retaining effective liquid sealing.

We claim:

1. A coupling for joining an ostomy bag to a pad of adhesive material which can be applied to the wearer of the bag comprising:
    (a) two coupling elements, each of which has a substantially cylindrical, hollow portion, said coupling elements being adapted to engage one another;
    (b) an annular flange which extends laterally from said substantially cylindrical, hollow portion of each of said coupling elements;
    (c) an internal, inwardly extending flexible sealing skirt which is an integral part of said cylindrical, hollow portion of one of said coupling elements, said sealing skirt being configured to engage and make sealing engagement with the external surface of said cylindrical, hollow portion of said other coupling element; and
    (d) a plurality of pins extending in an axial direction from each of said flanges, said pins each having a head and shank configuration adapted to engage with a similar pin on said other coupling element, whereby the combination of said sealing skirt and said pins provides an easily removable, yet easily sealable apparatus for an ostomy product.

2. The coupling for an ostomy bag of claim 1 wherein said pins have substantially cylindrical shanks.

3. The coupling for an ostomy bag of claim 2 wherein said pins have substantially spherical heads.

4. The coupling for an ostomy bag of claim 3 further comprising an ostomy bag affixed to the flange of one of said coupling elements, there being an opening in the wall of said ostomy bag, said flange surrounding said opening, whereby said coupling element, with said attached ostomy bag can be coupled to said other coupling element when said other coupling element is being worn, and whereby when said coupling elements are brought together in an axial direction with one said cylindrical, hollow portion extending inside said other cylindrical, hollow portion, said headed pins on said flange of one coupling element interdigitate with said headed pins on said flange of said other coupling element, whereby said two coupling elements are flexibly held together.

5. The coupling for an ostomy bag of claim 1 further comprising a pad of adhesive material affixed to the flange of one of said coupling elements, whereby said coupling element can be adhesively applied to the wearer of the bag.

6. The coupling for an ostomy bag of claim 1 further comprising an ostomy bag affixed to the flange of one of said coupling elements, there being an opening in the wall of said ostomy bag, said flange surrounding said opening, whereby said coupling element, with said attached ostomy bag can be coupled to said other coupling element when said other coupling element is being worn.

* * * * *